United States Patent [19]

Ferdinand et al.

[11] Patent Number: 5,064,215
[45] Date of Patent: Nov. 12, 1991

[54] SAFETY SKI BINDING

[75] Inventors: Platter Ferdinand, Laas, Italy; Rosenich Paul, Wien, Austria

[73] Assignee: TMC Corporation, Baar/Zug, Switzerland

[21] Appl. No.: 423,443

[22] PCT Filed: Feb. 1, 1989

[86] PCT No.: PCT/EP89/00082
§ 371 Date: Oct. 3, 1989
§ 102(e) Date: Oct. 3, 1989

[87] PCT Pub. No.: WO89/07476
PCT Pub. Date: Aug. 24, 1989

[30] Foreign Application Priority Data

Feb. 19, 1988 [AT] Austria ................................. 405/88

[51] Int. Cl.[5] .............................................. A63C 9/08
[52] U.S. Cl. ..................................... 280/612; 280/623
[58] Field of Search .............. 280/611, 612, 623, 613, 280/634, 616, 617, 618, 625

[56] References Cited

U.S. PATENT DOCUMENTS 4,387,307 6/1983 D'Antonio .......................... 280/612

FOREIGN PATENT DOCUMENTS 315037 5/1974 Austria .
0042762 12/1981 European Pat. Off. .
8303555 10/1983 World Int. Prop. O. .

Primary Examiner—Andres Kashnikow
Assistant Examiner—Richard Camby
Attorney, Agent, or Firm—Finnegan, Henderson, Farabow, Garrett & Dunner

[57] ABSTRACT

Safety ski binding with at least one transducer, converting the forces acting on the binding into electric signals, and an evaluation circuit, connected to the triggering device and the transducer, which evaluation circuit has a threshold circuit having at least two threshold values, the one output of which threshold circuit activates the triggering device, and has a timing circuit, which is in connection with the triggering device, the transducer or transducers being connected to the input of the threshold circuit and the input of the timing circuit. In order to be able to adapt the triggering characteristic of such a binding to the loading capacity of the user, it is provided that the timing circuit is formed by an oscillator (5) controllable in its frequency, and a counter (3) connected downstream of the latter, which counter is in connection via a comparator (9) with the triggering device, the counter (3) being connected to the threshold circuit (2) and able to be activated by a signal corresponding to a second, lower threshold value.

6 Claims, 1 Drawing Sheet

SAFETY SKI BINDING

BACKGROUND OF THE INVENTION

1. Field of the Invention

The invention relates to a safety ski binding.

2. Description of the Related Art

A safety ski binding which the measured-value pickups are connected by a multiplexer to a switchable amplifier and a clock generator, has become known from WO 81/00 358-A1. In this case, the amplifier controls a voltage-controlled oscillator, the output signals of which are counted in assigned counters, which emit a release signal to the triggering device if a certain counter reading is exceeded. In this case, the signals of the voltage-controlled oscillator are passed in each case to the counters assigned to the individual-measured pickups, the corresponding switching being performed by the clock generator.

Although this achieves a triggering speed dependent on the magnitude of the forces occurring, it entails the disadvantage that, even under extreme loads, a certain delay in the driving of the triggering device cannot be avoided. Thus, in such a case, due to the high signal level which the measured-value pickups supply, although the oscillator, controlled in its frequency, operates with a correspondingly high frequency, the driving of the triggering device cannot begin until the intended counter reading which is fixed for a triggering is reached. In extreme cases, however, this may lead to a delayed triggering and consequently to a considerable risk of injury for the skier.

SUMMARY OF THE INVENTION

The object of the invention is to avoid these disadvantages and to propose a safety ski binding in which the triggering characteristic can be adapted to the loadability of the user and in which an undelayed triggering is possible in the event of correspondingly high forces acting on the skier or the binding.

This is achieved according to the invention by the fact that the threshold circuit has, in a way known per se, at least two outputs controlled as a function of different threshold values, of which the output controlled by the highest threshold value drives the triggering device without delay and of which the second output, controlled by a lower threshold value, is connected to the counter of the timing circuit.

It is achieved by these measures that, in the case of a certain high level of the output signal of the transducer, the triggering device is driven without delay, whereas, in the case of signal values of the transducer which lie between a lower threshold, activating the timing circuit and the mentioned uppermost threshold, the triggering device is activated with a time delay, variable as a function of the magnitude of the signal supplied by the measured-value pickup. This ensures on the one hand an undelayed triggering of the binding under very high loads and on the other hand a load-dependently delayed triggering under loads in a certain range, as a result of which on the one hand false triggerings are avoided and on the other hand a particularly high degree of safety is ensured even under extreme loads.

In this context, it may also be provided that the threshold circuit is connected directly to a release input of the counter and to a reset input of the counter via an inverter and, if appropriate, to a monostable flip-flop, connected downstream of the latter and having a short operating time.

It is thus ensured that the counter is only activated when a signal exceeding the one threshold value occurs on the threshold circuit and a resetting of the counter takes place as soon as the signal drops below this level again, the flip-flop supplying a corresponding needle pulse.

In order to create defined conditions in particular in the case of very small and prolonged output signals of the transducer or transducers, according to a further feature of the invention it may be provided that the oscillator, variable in its frequency, can be changed between a frequency other than zero and a maximum frequency.

It is thus ensured that, in the case of loads just above the activation threshold of the counter, a triggering of the binding takes place within a certain time, essentially fixed by the minimum frequency of the oscillator, and as a result an endangerment to the health of the user by high loads over a considerable time period are (sic) avoided with certainty.

In this context, according to a further feature of the invention, it may be provided that the oscillator, variable in its frequency, is designed as a voltage-controlled oscillator, to which a settable voltage, corresponding to a minimum frequency, is applied.

As a result, the oscillator can be controlled directly by the output signals of the transducer or transducers, generally in the form of voltages.

According to a further feature of the invention, it may be provided that the output of the threshold circuit connected to the counter of the timing circuit is also connected to an input of an AND gate, the second input of which is connected to the output of the comparator connected downstream of the counter of the timing circuit, the output of the AND gate being connected to the triggering device.

These measures give rise to the advantage that a triggering only takes place if the counter reading of the timing circuit necessary for a triggering is reached and the output signal of the transducer still has a level lying above the threshold level of the threshold circuit intended for an activation of the timing circuit. It is thus avoided that a triggering can still occur at the instant when the load drops below an uncritical value, as a result of which no false triggerings occur.

The invention is now explained in more detail with reference to the drawing. In this, FIG. 1 diagrammatically shows an evaluation circuit for a ski binding according to the invention and FIG. 2 shows a diagram of the threshold values.

The measuring signal input is connected to transducers 21, which serve as converting means to convert the forces acting on the binding into corresponding electric signals and can be formed, for example, by strain gages or piezo elements or the like. These signals pass via a low-pass filter 7, which serve (sic) for the filtering-out of higher-frequency fluctuations of the measuring signal induced by vibrations of the skis, and a DC-coupled amplifier 1 to a threshold circuit 2, which classifies the incoming signals according to three threshold values and supplies signals to the corresponding outputs $A_0$, $B_0$ and $C_0$, as soon as the input signal has exceeded the corresponding threshold values, which can be set via the adjusting inputs $A_1$, $B_1$ and $C_1$. p It can be seen in this case from FIG. 2 that the threshold value A has the highest level, threshold value B the middle level and the threshold value C the lowest level. Depending on which level the signal coming from the transducer has, a signal appears at none of the outputs $A_0$ to $C_0$ or at one to three of the outputs. The former is the case if the level C is not exceeded and the latter if the level A is exceeded.

A timing circuit 23 having a frequency controlled oscillator (5), counter (3), and comparator (9) ensures that, in the case of loads just above the activation threshold of the counter, a triggering of the binding takes place within a certain time, essentially fixed by the minimum frequency of the oscillator, and as a result an endangerment to the health of the user by high loads over a considerable time period are (sic) avoided with certainty.

In this context, according to a further feature of the invention it may be provided that the oscillator, variable in its frequency, is designed as a voltage-controlled oscillator, to which a settable voltage corresponding to a minimum frequency is applied.

It is also advantageous if an upper threshold can be set on the exceeding of which the triggering device can be activated without delay.

BRIEF DESCRIPTION OF THE DRAWINGS

The invention is now explained in more detail with reference to the drawing, in which.

DESCRIPTION OF THE PREFERRED EMBODIMENT

The measuring signal input is connected to transducers (not shown), which convert the forces acting on the binding into corresponding electric signals and may be formed, for example, by strain gages or piezo elements or the like. These signals pass via a low-pass filter 7, which serve (sic) for the filtering-out of higher-frequency fluctuations of the measuring signal induced by vibrations of the skis and a DC-coupled amplifier 1 to a threshold circuit 2, which classifies the incoming signals according to three threshold values and supplies signals to the corresponding outputs $A_0$, $B_0$ and $C_0$, as soon as the input signal has exceeded the corresponding threshold values, which can be set via the adjusting inputs $A_1$, $B_1$ and $C_1$.

Figure 1:
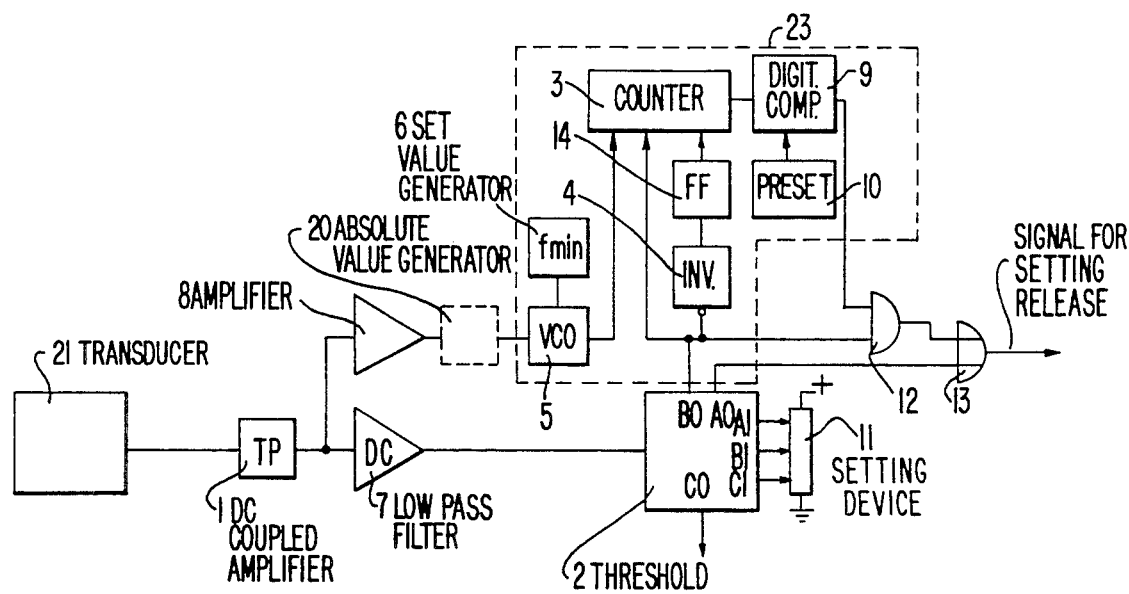
FIG. 1 diagrammatically shows an evaluation circuit for a ski binding according to the invention.
Figure 2:
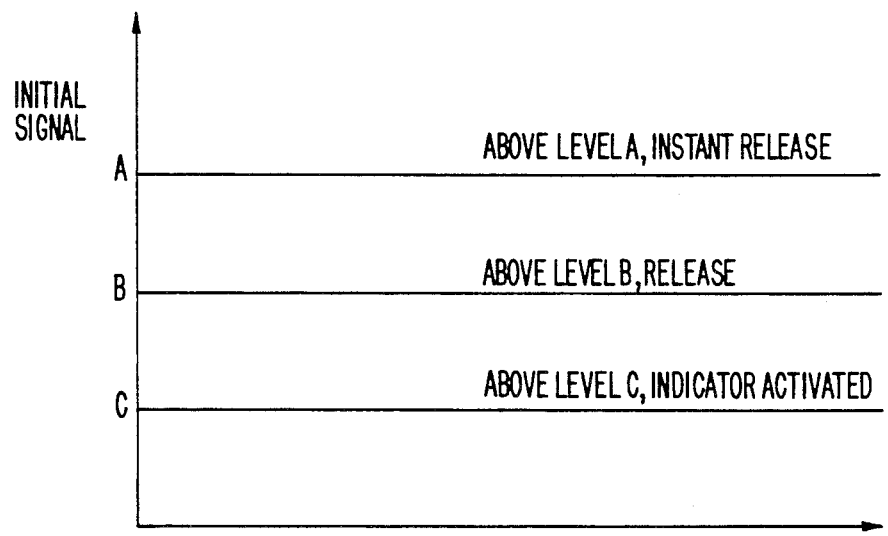
FIG. 2 shows a diagram of the threshold values.

It can be seen in this case from FIG. 2 that the threshold value A has the highest level, threshold value B the middle level and the threshold value C the lowest level. Depending on which level the signal coming from the transducer has, a signal appears at none of the outputs $A_0$ to $C_0$ or at one to three of the outputs. The former is the case if the level C is not exceeded and the latter if the level A is exceeded.

The output signals of the threshold circuit 2 which are associated with an exceeding of each of the previously defined levels of the input signals appear at separate outputs, it being possible, for example for the output $C_0$ to be connected to an indicator from which it can be ascertained whether the ski boot is held correctly in the binding, or for example there is an incorrect fit due to a layer of snow.

The output $B_0$ supplies a signal when an input signal is present which corresponds to a load which can only be tolerated for a relatively short time. This output is connected directly to a release input and via an inverter 4 and a monostable flip-flop 14, which is connected downstream of the latter, has only a short operating time and serves for the generation of a needle pulse, to a reset input of a counter 3. The latter receives its counting pulses from an oscillator controllable in its frequency, which is preferably designed as a voltage-controlled oscillator 5. However, the counter can only count the pulses of the oscillator as long as a release signal from the output $B_0$ of the threshold circuit 2 is available at the control input of the counter 3. If such a signal disappears from the output $B_0$, the inverter 4 emits a signal at its output and starts the monostable flip-flop 14, which, due to its short operating time, emits a needle pulse which resets the counter 3. It is thus ensured that the counter is reset until the occurrence once more of a signal at the output $B_0$ of the threshold circuit 2 and can begin immediately with counting.

This oscillator 5 is controlled by a set value generator 6 for a certain minimum frequency, which may be determined by a settable voltage source, and by the output signal of an amplifier 8, which is connected via a filter 7 to the measuring signal input, has a variable gain and is provided, for example, with a feedback network having diodes. In this case it may be provided that this amplifier 8 can be equipped with various feedback networks. This makes possible an adaptation of the triggering characteristic to the requirements of the user. If the measuring transducers emit positive and negative signals, an absolute-value generator 20 may be interposed between the amplifier 8 and the voltage-controlled oscillator 5, which generator only ever emits at its output voltage of one polarity, for example positive in relation to a reference potential, irrespective of the polarity of its input voltage relative to this reference potential.

The amplifier 8 supplies an output signal as a function of the input signal supplied by the transducers (not shown). This achieves the result that, as soon as the input signal exceeds the level B, and therefore the counter 3 is released, counting pulses are applied to the counter 3 as a function of the amplitude of the input signal or rise of the latter, and therefore its counter reading is incremented more or less quickly.

This counter reading is continuously compared by the comparator 9, connected to the output of the counter 3, with a predetermined value, which can be input to the comparator 9 via an input device 10. This input device is expediently arranged in such a way that it is only accessible to a competent attendant, the same applying to the setting device 11 for fixing the threshold values of the threshold device 2.

When the counter reading matches the predetermined comparison value, the comparator 9 emits a signal, which is fed via an AND element 12, the second input of which is connected to the output $B_0$ of the threshold circuit 2, and an OR element 13 to the triggering device (not shown). The second input of the OR element 13 is in this case connected to the output $A_0$ of the threshold circuit 2, so that, as soon as the level A of the input signal is exceeded, the triggering device is driven without delay.

If, on the other hand, only the level B is exceeded by the input signal, a driving of the triggering device takes place with a delay, which depends in the case of the exemplary embodiment presented on the amount of the amplitude of the input signal, or, if the input signal drops again below the level B before reaching the corresponding delay time, not at all.

In this way, triggerings of the binding under loads which, although relatively high, only last for a time which is not dangerous, are avoided.

As far as the AND element 12 is concerned, it should be noted that it is also possible to dispense with this and connect the output of the comparator 9 directly to an input of the OR element 13.

The arrangement of a set value generator 6 for the minimum frequency of the oscillator 5 makes it possible to limit correspondingly the maximum time up to a driving of the triggering device in the case of prolonged input signals which are only just above the level B, or only changed slowly.

The invention is, of course, not restricted to the exemplary embodiment presented, rather modifications of the same are conceivable. For instance, in the case of the exemplary embodiment presented, three threshold values are provided, but in principle their number is unrestricted, a better adaptation to the anatomical characteristics of the user being made possible with an increasing number of provided levels.

We claim:

1. A ski binding comprising:
   converting means for converting forces acting on the ski binding into an electric signal;
   means for triggering said ski binding; and
   an evaluation circuit electrically connected to said converting means and said triggering means, said evaluation circuit including
     a timing circuit having a controllable frequency oscillator, said timing circuit for receiving said electric signal from said converting means and for generating a triggering signal in response thereto, said timing circuit further including a comparator and a counter, said comparator and said counter being electrically connected to said oscillator, said counter for counting pulses of said oscillator, and said comparator for generating said triggering signal when said counted number of pulses exceeds said predetermined value; and
     a threshold circuit for receiving said electric signal from said converting means, and for generating a first output signal for transmission to said timing circuit and second output signal for transmission to said triggering means, said threshold circuit for generating said first output signal when said electric signal of said converting means is greater than a first threshold value, said threshold circuit for generating said second output signal when said electric signal of said converting means is above a second threshold value less than said first threshold value.

2. The ski binding of claim 1 wherein said evaluation circuit further comprises an inverter, a monostable flip-flop, and said counter includes a reset input and a release input, said threshold circuit being directly connected to the release input and the reset input of said counter via said inverter, and said monostable flip-flop having a short operating time and being connected to said threshold circuit.

3. The ski binding recited in claim 1 or claim 2 wherein said oscillator can be altered between a frequency other than zero and a maximum frequency.

4. The ski binding according to claim 3, wherein said oscillator is a voltage-controlled oscillator that generates a minimum frequency in response to a predetermined voltage applied thereto.

5. The ski binding according to claim 3, wherein said second output signal of said threshold circuit is supplied to the first of two inputs of an AND gate, the second input of said AND gate receives a signal from said comparator, and an output of said AND gates is connected to said triggering means.

6. A ski binding comprising:
   converting means for converting forces acting on the ski binding into an electric signal;
   means for triggering said ski binding; and
   an evaluation circuit electrically connected to said converting means and said triggering means, and including an inverter and a monostable flip-flop, said evaluation circuit further including
   a timing circuit having a controllable frequency oscillator, said timing circuit for receiving said electric signal from said converting means and for generating a triggering signal in response thereto, said timing circuit further including a comparator and a counter having a release input and a reset input, said comparator and said counter being electrically connected to said oscillator, said counter for counting pulses of said oscillator, and said comparator for generating said triggering signal when said counted number of pulses exceeds said predetermined value;
   a threshold circuit for receiving said electric signal from said converting means, and for generating a first output signal for transmission to said timing circuit and second output signal for transmission to said triggering means, said threshold circuit for generating said first output signal when said electric signal of said converting means is greater than a first threshold value, said threshold circuit for generating said second output signal when said electric signal of said converting means is above a second threshold value less than said first threshold value, said threshold circuit being directly connected to the release input and the reset input of said counter via said inverter, and said monostable flip-flop having a short operating time and being connected to said threshold circuit.

* * * * *

UNITED STATES PATENT AND TRADEMARK OFFICE
CERTIFICATE OF CORRECTION

PATENT NO. : 5,064,215

DATED : November 12, 1991

INVENTOR(S) : Ferdinand PLATTER et al.

It is certified that error appears in the above-identified patent and that said Letters Patent is hereby corrected as shown below:

Title page, Inventors, change "Platter Ferdinand" to --Ferdinand Platter-- and change "Rosenich Paul" to --Paul Rosenich--.

Claim 5, column 6, line 17, change "gates" to --gate--.

Signed and Sealed this

Sixteenth Day of March, 1993

*Attest:*

STEPHEN G. KUNIN

*Attesting Officer*     Acting Commissioner of Patents and Trademarks